US010087412B2

(12) United States Patent
Fuller (10) Patent No.: US 10,087,412 B2
(45) Date of Patent: Oct. 2, 2018

(54) **IN VITRO PROPAGATION OF *BABESIA MICROTI***

(71) Applicant: Fuller Laboratories, Fullerton, CA (US)

(72) Inventor: Lee Fuller, Fullerton, CA (US)

(73) Assignee: FULLER LABORATORIES, Fullerton, CA (US)

( * ) Notice: Subject to any disclaimer, the term of this patent is extended or adjusted under 35 U.S.C. 154(b) by 0 days.

(21) Appl. No.: 15/709,253

(22) Filed: Sep. 19, 2017

(65) Prior Publication Data

US 2018/0080004 A1    Mar. 22, 2018

Related U.S. Application Data

(60) Provisional application No. 62/396,697, filed on Sep. 19, 2016, provisional application No. 62/506,429, filed on May 15, 2017.

(51) Int. Cl.
*C12N 1/10* (2006.01)
*C12N 5/078* (2010.01)

(52) U.S. Cl.
CPC ............ *C12N 1/10* (2013.01); *C12N 5/0641* (2013.01); *C12N 2502/1128* (2013.01); *C12N 2502/1157* (2013.01)

(58) Field of Classification Search
CPC ........ A61K 2039/505; A61K 2039/507; A61K 39/3955; A61K 45/06; C07K 16/28; C07K 16/2803; C07K 16/2818; C07K 2317/21; C07K 2317/24; C07K 2317/34; C07K 2317/52; C07K 2317/56; C07K 2317/565; C07K 2317/73; C07K 2317/74; C07K 2317/76; C07K 2317/92; G01N 2333/20; G01N 2333/29; G01N 2333/43556; G01N 2333/44; G01N 2800/42; G01N 33/53; G01N 33/56905; G01N 33/56911; G01N 33/6893; Y10T 436/25; C12N 1/10; C12N 2502/1128; C12N 2502/1157; C12N 5/06
See application file for complete search history.

(56) References Cited

U.S. PATENT DOCUMENTS

| 4,314,026 A * | 2/1982 | Descamps-Latscha ...................... C12Q 1/66 422/52 |
|---|---|---|
| 5,824,537 A | 10/1998 | Mahl et al. |
| 2013/0177941 A1 | 7/2013 | Hoey et al. |
| 2015/0297572 A1* | 10/2015 | Niazi ..................... A61K 31/16 514/375 |

FOREIGN PATENT DOCUMENTS

WO    WO 2018/053432 A1    3/2018

OTHER PUBLICATIONS

Chen et al. Parasitol. International 48: 223-231, 2000.*
Taylor et al. Infect. Immun. 32: 563-570, 1981.*
Walker Mol. Chem. Neuropathol. 34: 197-218, 1998.*
Gagnon, P., et al., Purification of IgM Monoclonal Antibodies, BioPharm International Supplement, 10 pages, Mar. 2008.
Gagnon, P., et al., IgM Purification with Hydroxyapatite, BioProcess International, Accessible on the world wide web at http://www.bioprocessintl.com/upstream-processing/biochemicals-raw-materials/igm-purification-with-hydroxyapatite-349783, Feb. 1, 2014, Accessed Dec. 19, 2017.
IgM Purification Kit Instructions, Thermo Scientific, 2011.
Nevens, J.R., et al., Affinity chromatographic purification of immunoglobulin M antibodies utilizing immobilized mannan binding protein, Journal of Chromatography, vol. 597, Nos. 1-2, pp. 247-256, 1992.
Nethery, A., et al., Single-step purification of immunoglobulin M C1q-Sepharose, Journal of Immunological Methods, vol. 126, No. 1, pp. 57-60, 1990.
Ohta, M., et al., The mechanism of carbohydrate-mediated complement activation by the serum mannan-binding protein, Journal of Biological Chemistry, vol. 265, No. 4, pp. 1980-1984, 1990.
Bautista, C.R., et al., Effect of Immune Serum on the Growth of Babesia microti in Hamster Erythrocytes in Short-Term Culture, Infection and Immunity, vol. 25, No, 1, pp. 470-472, 1979.
Birmingham, D.J., et al., The complex nature of serum C3 and C4 as biomarkers of lupus renal Flare, Lupus, vol. 19, No. 11, pp. 1272-1280, 2010.
Borggraefe, I., et al. Babesia Microti Primarily Invades Mature Erythrocytes in Mice, Infection and Immunity, vol. 74, No. 6, pp. 3204-3212, 2006.
Burkhardt, M.A., et al., Synergistic interactions of blood-borne immune cells, fibroblasts and extracellular matrix drive repair in an in vitro peri-implant wound healing model, Scientific Reports, vol. 6, pp. 1-15, 2016.
Goldfarb, A.R., et al., Characterization of Neuropathies Associated with Elevated IgM Serum Levels, Journal of the Neurological Sciences, vol. 228, pp, 155-160, 2005.
Inchley, C.J., The contribution of B-cell proliferation to spleen enlargement in Babesia rnicroti-infected Mice, Immunology, vol. 60, No. 1, pp. 57-61, 1987.
International Search Report and Written Opinion, dated Jan. 18, 2018, in International Application No. PCT/US2017/052075.
Jack, R.M., et al., Babesia Rodhani Interactions with Complement Relationship to Parasitic Entry Into Red Cells, The Journal of Immunology, vol. 124, pp. 1566-1573, 1980.
Lai A Fat, R.F.M., et al., In Vitro Synthesis of Some Complement Components (C1q, C3 and C4) by Lymphoid Tissues and Circulating Leucocytes in Man, Immunology, vol. 28, pp. 359-368, 1975.
Schuster, F.L., Cultivation of Babesia and Babesia-Like Blood Parasites: Agents of an Emerging Zoonotic Disease, Clinical Microbiology Reviews, vol. 15, No. 3, pp. 365-373, 2002.
Ward, P.A., et al., The Entry Process of Babesia Merozoites into Red Cells, American Journal of Pathology, vol. 102, No. 1, pp. 109-113, 1981.
Whitlock, C.A., et al., Long-Term Culture of B Lymphocytes and their Precursors from Murine Bone Marrow, Proceedings of the national Academy of Sciences U.S.A., vol. 79, No. 11, pp. 3608-3612, 1982.

* cited by examiner

*Primary Examiner* — Sarvamangala Devi
(74) *Attorney, Agent, or Firm* — Knobbe, Martens, Olson & Bear, LLP (57) ABSTRACT

A method for continuous in vitro propagation of *Babesia microti* and *microti*-like species is disclosed. The method comprises incubating *B. microti* in culture medium comprising host erythrocytes in the presence of a source of complement and a source of anti-*B. microti* IgM antibody. In one embodiment, the source of anti-*B. microti* IgM antibody is substantially free of IgG antibody. In one embodiment, the source of complement is a cell or cell line that secretes complement.

14 Claims, 2 Drawing Sheets

FIG. 1

FIG. 2A  FIG. 2B  FIG. 2C  FIG. 2D

IN VITRO PROPAGATION OF *BABESIA MICROTI*

CROSS REFERENCE TO RELATED APPLICATIONS

This application claims the benefit of U.S. Provisional Application No. 62/396,697, filed on Sep. 19, 2016 and U.S. Provisional Application No. 62/506,429, filed on May 15, 2017, which are hereby incorporated by reference in their entireties.

BACKGROUND

Field

The present disclosure is generally related to methods for the continuous in vitro propagation of *Babesia microti* ("*B. microti*") and related "*microti*-like" hemoparasite species.

Description of the Related Art

*B. microti* was originally described by Victor Babes in 1885 and has been increasingly recognized as a human pathogen since then.

SUMMARY

A method for in vitro propagation of *Babesia microti* is disclosed. The method includes incubating *B. microti* in culture medium comprising host erythrocytes in the presence of a source of complement and a source of anti-*B. microti* IgM antibody.

In one variation, the *B. microti* is propagated continuously for more than one passage. In another variation, the *B. microti* is propagated continuously for at least 200 hours.

In another variation, the source of IgM anti-*B. microti* antibody is substantially free of IgG antibody. The source of anti-*B. microti* IgM antibody may be from the same species as the host erythrocytes.

In one embodiment, the source of complement comprises a cell or cell line that is co-cultured with the host erythrocytes, wherein the cell or cell line secretes complement into the culture medium. The cell or cell line may be selected from the group consisting of murine PD388D1, hamster NIL-8 embryonic fibroblasts, balb/c 3T3 fibroblasts, alveolar type II epithelial cells A549, canine DH82, human THP-1, human HL60, human HeLa 229, HSB-2 lymphocytic leukemia, and monocytic leukemia cell line. In one variation, the cell or cell line is a mammalian cell or cell line selected from the group consisting of human THP-1, human HL60, human HeLa 229, HSB-2 lymphocytic leukemia, and monocytic leukemia cell line. In another variation, the cell or cell line is derived from human monocyte/macrophage lineage selected from THP-1, HL60 or AML-193. In another variation, the cell or cell line is derived from human endothelial cells, human hepatic cells, human gastrointestinal cells, human epithelial cells, human alveolar cells, murine PD388D1, hamster NIL-8 embryonic fibroblasts, BALB/c 3T3 fibroblasts, or alveolar type II epithelial cells A549. In some embodiments, the source of complement comprises peripheral blood mononuclear cells (PBMCs).

In another embodiment, the cell or cell line is co-cultured with the host erythrocytes either together or separately using a transwell system.

In one embodiment, the source of IgM antibody is selected from the group consisting of splenic lymphocytes, B cells, plasma cells, plasmablasts, and hybridomas.

In another embodiment, the source of complement is added exogenously to the culture medium. The complement may be added by an automated device.

A method is disclosed for continuous in vitro propagation of *B. microti*-related hemoparasites, the method comprising incubating the *B. microti*-related hemoparasites in culture medium comprising host erythrocytes in the presence of a source of complement and a source of anti-*B. microti*-related hemoparasite IgM antibody.

The *B. microti*-related hemoparasites may be selected from the group consisting of *B. microti sensu lato, B. rodhaini, Theileria annae* (Spanish canine pathogen), and *B. microti*-like spp A propagated culture comprising *B. microti* is disclosed in accordance with another embodiment. The culture comprises culture medium comprising host erythrocytes in the presence of a source of complement and a source of anti-*B. microti* IgM antibody.

The propagated culture may be substantially free of IgG antibody.

In one embodiment of the propagated culture, the host erythrocytes are selected from human, mouse, hamster or other permissive host.

In a variation to the propagated culture, the source of complement is from the same species as the host erythrocytes. In another variation, the source of anti-*B. microti* IgM antibody is from the same species as the host erythrocytes.

BRIEF DESCRIPTION OF THE DRAWINGS

FIG. 1 shows the effect of serum complement supplementation on *B. microti* growth. Controls without supplement throughout are depicted by (■), while another set of controls supplemented only at 4 hours with 2% complement (8×—refers to 8 times more than the 0.25% used for other supplement concentrations) are depicted by (●) (i.e., it is 8 times the concentration of the other supplementations and only added once at 4 hour mark). Supplements of 0.25% complement at 4, 8 and 12 hours are depicted by (▲), while (♦) depict supplementation with 0.25% complement at 8 and 12 hours, and (□) depict 0.25% supplemented only at 12 hours.

FIG. 2A-FIG. 2D show Giemsa stained thin smears of in vitro cultivated *B. microti*, Westport strain, passage 18. Scale bars=7 μm.

FIG. 2A shows a Maltese cross form indicative of peak replication.

FIG. 2B shows typical ring forms, one (bottom left) with a white feeding vacuole.

FIG. 2C shows lower magnification field demonstrating 4 of 22 cells parasitized.

FIG. 2D shows multiple parasites within a single cell.

DETAILED DESCRIPTION

Despite major advances in propagating parasites belonging to various species of the genus *Babesia*, the species *microti* remains one of those requiring animal passage in hamsters and/or mice for propagation. Skilled researchers have combined to spend many years of intense effort in seeking continuous propagation of this single species in vitro, all without success.

The present disclosure relates to methods for the in vitro propagation of B. microti in one or more host cells. In some embodiments, the disclosure relates to methods for the continuous in vitro propagation of B. microti. "Continuous" in vitro propagation, or culture of B. microti, means propagation for more than a single passage. In some embodiments, a "passage" means diluting a culture having an original number of parasites (i.e., an original level of infection, percent infection, or "parasitemia") and allowing the number of parasites in the diluted culture to increase by cell division until the number of parasites returns to its original level. For example, a culture may be diluted 1:4 i.e., to $\frac{1}{4}^{th}$ of the original number of parasites. Thus, in some embodiments, more than a single passage means after being diluted 1:4 (or another dilution factor as determined by one of ordinary skill in the art based on the level of infection), the culture returns to its original ("pre-passage") percent infection. In some embodiments, "continuous" refers to propagation for several passages. In some embodiments, "continuous" refers to propagation for more than about 1 to about 100 passages. In some embodiments, "continuous" refers to long-term propagation for about 1 day to about 7 days, about 1 week to about 4 weeks, about 1 month to about 12 months, and/or about 1 year to about 5 years.

In some embodiments, "continuous" in vitro propagation over the short-term refers to at least 200 hours of propagation. In some embodiments, "continuous" in vitro propagation over the short-term refers to about 200 hours of propagation. In some embodiments, "continuous" in vitro propagation over the short-term refers to more than 200 hours of propagation. In some embodiments, "continuous" in vitro propagation over the short-term refers to about 100 hours to about 10,000 hours of propagation.

Without being bound by any theory, it is believed that failure of continuous propagation of B. microti is due to the inability of the parasites to efficiently translate their intracellular divisions into subsequent penetration of uninfected host cells. For example, when parasites from hamster and/or mouse were coated with IgM and complement, even though the parasites underwent several folds of cellular division, the daughter parasites could not penetrate new uninfected host cells if the IgM and/or complement coating the maternal parasites were degraded or if neither IgM nor complement was available to coat the daughter parasites.

Without being bound by any theory, continuous propagation requires infected host cells to be diluted with uninfected host cells in fresh medium, which need to be added on a regular basis. In some embodiments, parasites can be purified by lysis of infected host cells (e.g., host erythrocytes) and then returned to culture with uninfected host erythrocytes. However, this is not necessary for continuous propagation.

In some embodiments, in vitro cultures were begun with a very rich base medium to which two unusual components were added. In some embodiments, an HL-1 medium base medium (Lonza, Walkersville, Md.) was supplemented with 20-40% unheated fetal bovine serum, 2 mM glutamine dipeptide (Gibco), 100 μg/ml gentamicin sulfate, 1 mg/ml AlbuMAX II (Gibco), 1×HT Supplement (Gibco), 1×HB-101 Supplement (Irvine Scientific, Irvine, Calif.), 1 mM L-cysteine-HCl, 0.02 mM bathocuproine-disulfonic acid (BCS, Sigma Chemical) and 1× Antibiotic-Antimycotic (Gibco). In some embodiments, cultures have included the addition and/or blending of human and/or hamster serum with fetal bovine serum (FBS), but the additional effects did not warrant the additional cost incurred. In some embodiments, two unusual components were added to the base medium, namely, a source of complement and a source of IgM.

Figure 1:
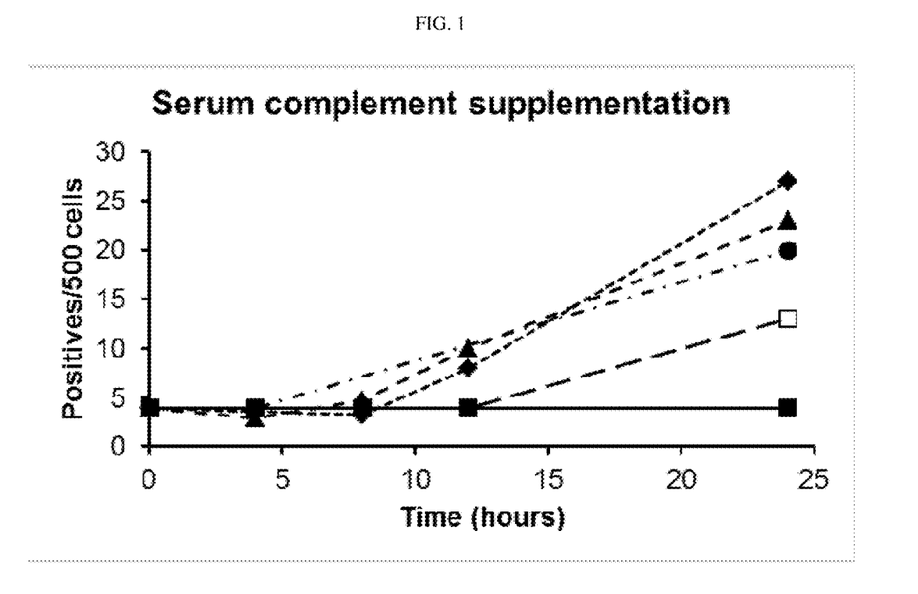
Figure 2A:
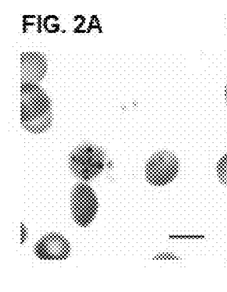
Figure 2B:
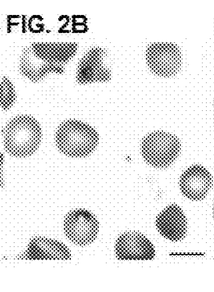
Figure 2C:
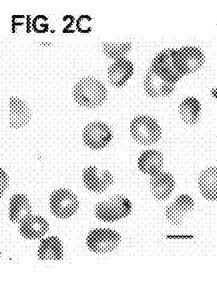
Figure 2D:
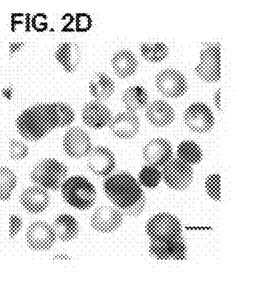

In some embodiments, to this base medium was added flash-frozen hamster or human serum (Innovative Research, Novi, Mich.) from aliquots stored at −80° C. This serum is sold as "Hamster Complement" and "Human Complement". The serum acts as a source of complement. In some embodiments, dilutions for use are determined by trials using serial dilutions in 24-well tissue culture trays. In some embodiments, short-term experiments have used 1:400 dilutions (about 0.25% fresh serum), although low levels of continuous infection are usually observed at that level of serum (i.e., complement source). Higher levels of infection are obtained by frequent serum (complement) supplementation, for example, every 4 hours or less (FIG. 1). In some embodiments, at a level of approximately 1-2% serum a 24-hour cycle may be completed without supplementation or with medium change every 12 hours (FIG. 1).

In some embodiments, a source of IgM was added to the base medium. In some embodiments, a source serum or plasma for IgM class polyclonal antibody to B. microti is obtained from positive donor units (e.g., human) and hamsters infected with B. microti. In some embodiments, the source serum or plasma is a source of IgM class monoclonal antibody to B. microti.

In view of the limitations on obtaining blood from active B. microti-infected hamsters as a source of polyclonal IgM antibody, in some embodiments, cloned IgM monoclonal antibodies from the spleen lymphocytes of B. microti-infected BALB/c mice can be used. For example, Immuno-Precise Antibodies, Ltd., Victoria, BC is supplied with spleen lymphocytes of B. microti-infected BALB/c mice to generate hybridoma fusions to generate cloned IgM monoclonal antibodies. In some embodiments, one or more other sources of IgM can be used. Non-limiting examples include B cells, plasma cells, plasmablasts, hybridomas, etc. Accordingly, in some embodiments, the use of such cloned IgM monoclonal antibodies should simplify and standardize the in vitro propagation of B. microti. In some embodiments, polyclonal IgM antibody is used. In some embodiments, monoclonal IgM antibody is used. In some embodiments, both polyclonal and monoclonal IgM antibodies are used. In some embodiments, IgM antibodies are from the same species (i.e., syngeneic). In some embodiments, IgM antibodies may be from a different species (i.e., allogeneic). In some embodiments, erythrocytes, complement, and IgM are obtained from the same host. In some embodiments, erythrocytes, complement, and IgM are obtained from one or more different hosts (e.g., human, hamster, and mouse).

Anti-B. microti IgG antibodies compete with IgM antibodies. The IgG antibodies opsonize the B. microti in vivo, leading to clearance of B. microti by macrophages. In some embodiments, the clearance by macrophages leads to low yields of parasites in cultures.

Without being bound by any particular theory, it is believed that anti-B. microti IgG antibodies are detrimental to the rate of propagation of culture. Without being limited to any particular theory, it is believed that in the case of propagation in the presence of macrophages, IgG antibodies cause opsonization and phagocytosis by macrophages of the trophozoite stage of the parasite. Thus, without being limited to any particular theory, it is believed that the percent IgG in the culture is inversely proportional to the percent parasite yield, both due to the inability of IgG-opsonized parasites to penetrate/infect fresh erythrocytes and, when macrophages are not present in the culture, by competition with the IgM antibodies that enable parasites to penetrate/infect fresh erythrocytes.

Thus, in some embodiments, the source of anti-*B. microti* IgM antibody is substantially free of IgG antibodies. In some embodiments, the source of anti-*B. microti* IgM antibody is rendered substantially free of IgG by using one or more commercially available IgG removal kits known in the art. In some embodiments, the source of anti-*B. microti* IgM antibody has no IgG, or no detectable IgG. In some embodiments, the source of anti-*B. microti* IgM antibody has less than about 0.0001%, 0.001%, 0.01%, 0.1%, or 1% IgG. In some embodiments, the source of anti-*B. microti* IgM antibody has less than about 0.1%, 0.2%, 0.3%, 0.4%, 0.5%, 0.6%, 0.7%, 0.8%, 0.9%, 1%, 5% or 10% IgG, or a value within a range defined by any two of the aforementioned values. In some embodiments, the source of anti-*B. microti* IgM antibody has any percentage between about 0.0001 and 10% IgG. In some embodiments, the source of anti-*B. microti* IgM antibody is completely free of IgG antibodies. Thus, in some embodiments, the source of anti-*B. microti* IgM antibody has 0% IgG antibody.

In some embodiments, IgM from serum or plasma is precipitated as cryoglobulin. In some embodiments, the precipitation is performed by overnight dialysis at 2-8° C. against a suitable dialysis buffer. In some embodiments, the dialysis buffer is a potassium phosphate buffer, 10 mM pH 5.4. In some embodiments, one or more other dialysis buffers can be used by one of ordinary skill in the art. In some embodiments, the cryoglobulin is washed with cold dialysis buffer and then dissolved in buffered saline. In some embodiments, an acetate buffered saline (10 mM acetate pH 5.4) is used to dissolve the cryoglobulin. As even semi-purified IgM is notoriously unstable, it is mixed with an equal volume of IgM Stabilizing Diluent (2×—refers to 2 times more than the other examples) and maintained at 2-8° C. IgM Stabilizing Diluent (1×) consists of 20% sorbitol and 1 M glycine in 50 mM acetate buffer (pH 5.5). This stabilized IgM solution could not be used at less than a 1:50 dilution in medium due to its negative effects on the erythrocytes and its use dilution was determined by multiple in vitro culture trials using serial dilutions. In some embodiments, after longer-term experience, the use dilution has dropped from 1% to be approximately equal to the IFA titer of the stabilized IgM (1:400).

In some embodiments, the concentration of polyclonal IgM that supports in vitro propagation of *Babesia* species ranges from about 0.001 µg/ml to about 100 µg/ml. In some preferred embodiments, the concentration of polyclonal IgM that supports in vitro propagation of *Babesia* species ranges from about 0.01 µg/ml to about 10 µg/ml. In some embodiments, polyclonal IgM at a concentration range of 0.001 µg/ml to about 100 µg/ml supports in vitro propagation of *Babesia* for about 2 days to about 4 days with a doubling time of about 24 hours. In some preferred embodiments, polyclonal IgM at a concentration range of about 0.01 µg/ml to about 10 µg/ml supports in vitro propagation of *Babesia* for about 4 days with a doubling time of about 12 hours.

In some embodiments, the concentration of monoclonal IgM that supports in vitro propagation of *Babesia* species ranges from about 0.005 µg/ml to about 500 µg/ml. In some preferred embodiments, the concentration of monoclonal IgM that supports in vitro propagation of *Babesia* species ranges from about 0.05 µg/ml to about 50 µg/ml. In some embodiments, monoclonal IgM at a concentration range of about 0.005 µg/ml to about 500 µg/ml supports in vitro propagation of *Babesia* for about 2 days to about 4 days with a doubling time of about 24 hours. In some preferred embodiments, monoclonal IgM at a concentration range of about 0.05 µg/ml to about 50 µg/ml supports in vitro propagation of *Babesia* for about 4 days with a doubling time of about 12 hours.

In some embodiments, a blend of different clones of IgM antibodies (i.e., a combination of more than one clone of IgM antibody) is used for in vitro growth of *Babesia*. In some embodiments, a blend of different clones of IgM antibodies supports in vitro growth of *Babesia* more efficiently as compared to the different clones of IgM antibodies used individually. In some embodiments, a blend of different clones of IgM antibodies is about 10% to about 90% more efficient as compared to the different clones of IgM antibodies used individually. In some embodiments, a blend of different clones of IgM antibodies is about 10, 20, 30, 40, 50, 60, 70, 80, 81, 82, 83, 84, 85, 86, 87, 88, 89, or 90% more efficient as compared to the different clones of IgM antibodies used individually, or a value within a range defined by any two of the aforementioned values. In some embodiments, clonal mixtures of different IgM antibodies are used for in vitro growth of *Babesia*. In some embodiments, the optimum concentration of the different clones of IgM antibodies can be determined by one of ordinary skill in the art using standard techniques known in the art (e.g., ELISA).

In some embodiments, at least two IgM monoclonal antibodies with different epitope specificities are used support in vitro *Babesia* growth at the same level as polyclonal IgM. In some embodiments, 2 to about 20 IgM monoclonal antibodies with different epitope specificities are used support in vitro *Babesia* growth at the same level as polyclonal IgM.

In some embodiments, hybridoma supernatant is a source of monoclonal IgM. In some embodiments, the hybridoma supernatant is diluted and used as a source of monoclonal IgM. In some embodiments, the hybridoma supernatant is diluted 20% v/v to about 60% v/v and used as a source of monoclonal IgM. In some embodiments, the concentration of IgM in the hybridoma supernatant that supports in vitro *Babesia* growth ranges from about 0.2 µg/ml to about 200 µg/ml. In some embodiments, the concentration of IgM in a diluted hybridoma supernatant that supports in vitro *Babesia* growth ranges from about 2 µg/ml to about 4 µg/ml. In some embodiments, the concentration of IgM in a diluted hybridoma supernatant that supports in vitro *Babesia* growth ranges from about 4 µg/ml to about 6 µg/ml. In some embodiments, the concentration of IgM in a diluted hybridoma supernatant that supports in vitro *Babesia* growth ranges from about 6 µg/ml to about 12 µg/ml.

In some embodiments, one or more commercial grade IgM purification methods can be utilized to produce milligram quantities for the embodiments of the methods described herein. Non-limiting examples include kits based on immobilized mannan-binding proteins (as described in Nevens, J. R., et al., Affinity chromatographic purification of immunoglobulin M antibodies utilizing immobilized mannan binding protein, J Chrom (1992) 597:247-256; Nethery, A., et al, Single-step purification of immunoglobulin M on C1q-Sepharose, J Immunol Meth (1990) 126:57-60; Ohta, M., et al, The mechanism of carbohydrate-mediated complement activation by the serum mannan-binding protein, J Biol Chem (1990) 265:1980-1984, which are hereby incorporated by reference in their entireties), hydroxyapatite-based purification (bioprocessintl.com/upstream-processing/bio-chemicals-raw-materials/igm-purification-with-hydroxy-apatite-349783/, which is hereby incorporated by reference in its entirety), and sepharose-based purification (as described in labs.mcb.harvard.edu/Gaudet/Resources_Files/ GEHealthcare_chromatography/Don %27t%20move/ 18103746AA.pdf, which is hereby incorporated by reference in its entirety). Other advances in separation and purification of monoclonal antibodies would be known to one of ordinary skill in the art, for example, as described in bioprocessintl.com/upstream-processing/biochemicals-raw-materials/igm-purification-with-hydroxyapatite-349783/, which is hereby incorporated by reference in its entirety.

In some embodiments, the method comprises a co-culture method. In some embodiments, the co-culture method allows the cultures to progress without the need to add complement on a daily basis. In some embodiments, the co-culture method comprises one or more cells (e.g., primary cells) or cell lines (e.g., "primary" or continuous cell lines) as a source of one or more complement factors. In some embodiments, the complement factor is an active complement factor. In some embodiments, the source of complement is a cell or cell line that produces complement continuously. In some embodiments, the source of complement is a primary cell or cell line. In some embodiments, the primary cell or cell line produces complement continuously. In some embodiments, the primary cell or cell line produces complement indefinitely as long as the culture medium is changed every 2-3 days. In some embodiments, the primary cell or cell line produces and secrete complement factors. In some preferred embodiments, the complement-producing primary cell or cell line is from the same species as the source of erythrocytes used in the culture. In some embodiments, the source of complement is monocytic leukemia cell lines that produce complement continuously. In some embodiments, the cell or cell line that is the source of one or more complement factors is co-cultured with host erythrocytes either together or separately with a filter-mediated interface (e.g., using a transwell system).

In some embodiments, the source of complement is a source of complement factor C3. Without being bound by any theory, it is believed that parasite-bound IgM molecules are in turn bound by one or more molecules of complement factor C3 which then attach to one or more C3 receptors on erythrocytes. Without being bound by any theory, it is believed that the IgM-class antibody to *B. microti* fixes complement factor C3, which initiates the "alternate complement pathway." In this pathway, C3 binds the pentameric IgM molecules and is spontaneously cleaved into C3a and C3b. There is an erythrocyte receptor (CR1) for C3b (and C4b) that the IgM-C3 complex can attach to. The sheer multiplicity of this binding is necessary for and allows entry of the parasite into the erythrocyte. The erythrocyte receptors (CR1) are embedded in a fluid membrane and migrate to the initial attachment site to multiply the overall effect many-fold.

In some embodiments, it is contemplated that any cell or cell line that can secrete or synthesize and secrete with or without stimulus complement factor C3 can be used in the co-culture. In some embodiments, the source of complement is any cell or cell line that can secrete or synthesize and secrete with or without stimulus complement factor C3. In some embodiments, the cell or cell line that can secrete or synthesize and secrete with or without stimulus complement factor C3 is selected from the group consisting of murine PD388D1, hamster NIL-8 embryonic fibroblasts, balb/c 3T3 fibroblasts, alveolar type II epithelial cells A549, canine DH82, human THP-1, human HL60, human HeLa 229, HSB-2 lymphocytic leukemia, and monocytic leukemia cell line. In some embodiments, the source of complement comprises peripheral blood mononuclear cells (PBMCs). In some embodiments, a stimulus for the cell or cell line to secrete or synthesize and secrete complement factor C3 is well known in the art. For example, without being limiting, there are many ways to stimulate macrophages or other complement-secreting cells or cell lines, depending on the particular cell type and based on the natural and/or pharmaceutical inducers of complement secretion by the particular cell type. For example, in some embodiments, for macrophage/monocyte cell lines, PMA (phorbol 12-myristate 13-acetate) is used to induce a macrophage phenotype, and phenylephrine is used to further stimulate the production of chemokines and complement.

In some embodiments, the one or more complement-producing cells or cell lines used for the co-culture method are murine PD388D1, hamster NIL-8 embryonic fibroblasts, balb/c 3T3 fibroblasts, alveolar type II epithelial cells A549, canine DH82, human THP-1, human HL60, human HeLa 229, HSB-2 lymphocytic leukemia, and monocytic leukemia cell line. In some embodiments, the source of complement is selected from the group consisting of human THP-1, human HL60, human HeLa 229, HSB-2 lymphocytic leukemia, and monocytic leukemia cell line. In some embodiments, the cell or cell line is a mammalian cell or mammalian cell line. In some embodiments, the cell or cell line is a human cell or human cell line. In some embodiments, the human cell or cell line is a source of human complement. In some embodiments, the cell or cell line is a non-human cell or non-human cell line. In some embodiments, the source of complement comprises peripheral blood mononuclear cells (PBMCs).

In some embodiments, the number of complement-producing cells required is experimentally determined for each cell or cell line. In some embodiments, the number of complement-producing cells required is experimentally determined for each cell or cell line based on the desired results. In some embodiments, the number of complement-producing cells in the co-culture ranges from about $1 \times 10^3$/mL to about $1 \times 10^5$/mL. In some embodiments, the number of complement-producing cells in the co-culture ranges from about $1 \times 10^5$/mL to about $1 \times 10^8$/mL. In some embodiments, the number of complement-producing cells in the co-culture ranges from about $1 \times 10^8$/mL to about $1 \times 10^{10}$/mL. In some embodiments, the number of complement-producing cells in the co-culture is about $1 \times 10^2$/mL, $1 \times 10^3$/mL, $1 \times 10^4$/mL, $1 \times 10^5$/mL, $1 \times 10^6$/mL, $1 \times 10^7$/mL, $1 \times 10^8$/mL, $1 \times 10^9$/mL, or $1 \times 10^{10}$/mL, or a value within a range defined by any two of the aforementioned values. In some embodiments, the cells or cell lines possess an active metabolic and/or biochemical phenotype. In some embodiments, the cells or cell lines possess an active metabolic and/or biochemical phenotype, for example, similar to a macrophage.

In some embodiments, one or more complement factors are not provided by one or more cells or cells lines in the culture. In some embodiments, the use of other sources of complement other than a cell or cell line is also contemplated. Non-limiting examples include plasma, serum, and commercially available purified complement proteins. In some embodiments, one or more complement factors are exogenously added to the culture. For example, in some embodiments, complement factor C3 or C3b is exogenously added to the culture. In some embodiments, one or more complement factors are manually added to the culture. In some embodiments, one or more complement factors are added to the culture in an automated manner. In some embodiments, one or more complement factors are added to the culture in an automated manner using an automated machine. In some embodiments, one or more complement factors are added to the culture in an automated manner using an automated machine wherein the machine can be programmed to add one or more complement factors in a timed manner. In some embodiments, the machine can be programmed to add one or more specific amounts of one or more complement factors in a timed manner.

In some embodiments, complement factors are provided as one or more frozen pellets that are dispensed into a stream of medium entering the culture. In some embodiments, the one or more frozen pellets are dispensed into a stream of medium entering the culture and are provided in the culture at a desired concentration. In some embodiments, the one or more frozen pellets are manually dispensed into a stream of medium entering the culture and provided in the culture at a desired concentration. In some embodiments, the one or more frozen pellets are dispensed using a machine in automated manner into a stream of medium entering the culture and provided in the culture at a desired concentration.

In some embodiments, the fraction of infected erythrocytes (expressed as "parasitemia") in the culture ranges from about 0.001% to about 80%. In some embodiments, the presence of the source of complement improves the parasitemia by about 4-fold to about 10-fold. In some embodiments, the improvement in parasitemia is based on the strain of *B. microti* being propagated. In some embodiments, the strain of *B. microti* is selected from the group consisting of *B. microti* sensu stricto including strains GI, Westport and RMNS, *B. microti* sensu law (*microti*-like) including strains Awl (Kobe), Ho234 (Hobetsu). And other *microti*-like species include *B. rodaini* and "Spanish dog/canine pathogen" (previous known as *Theileria annae*). In some embodiments, the present disclosure can be applicable to other species of *Babesia*. Non-limiting examples include rodent parasite *B. rodhaini*, canine species of *Babesia* and *B. vulpes*. In some embodiments, any of the methods provided herein can also be adapted by one of ordinary skill in the art for any *B. microti*-like spp. Other *microti*-like parasites are included among these. For example, without being bound by any theory, it is believed that the *microti* group will emerge as a new genus following complete genome sequencing and analysis. Thus, other parasites within this new genus that are classified and/or re-classified following availability of additional sequencing data are also included.

In some embodiments, depending on the culture conditions, the doubling time of *Babesia* can range from less than about 12 hours to about 24 hours. In some embodiments, the doubling time ranges from about 8 hours to about 24 hours. In some embodiments, the doubling time is about 6, 7 8, 9, 10, 11, 12, 13, 14, 15, 16, 17, 18, 19, 20, 21, 22, 23 or 24 hours, or a value within a range defined by any two of the aforementioned values.

In some embodiments, the *Babesia* species are related both genetically and by common means of entry into erythrocytes, and therefore, amenable to continuous propagation by embodiments of methods described here. Thus, in some embodiments, the embodiments of the methods described herein encompass the entire group of closely related *microti*-like (*microti* group) hemoparasites currently within the genus *Babesia*, including both *Babesia microti sensu stricto* and *sensu lato*. These currently include Japanese strains Awl (Kobe), Ho234 (Hobetsu), *Babesia vulpes* (previously *Theileria annae* or "Spanish dog"), *Babesia rodhaini*, *Babesia felis*, and others. In some embodiments, any *B. microti*-like spp is amenable to continuous propagation by embodiments of methods described here.

Additional Embodiments

In some embodiments, a method for in vitro propagation of *Babesia microti*, the method comprising incubating *B. microti* in culture medium comprising host erythrocytes in the presence of a source of complement and a source of anti-*B. microti* IgM antibody. In some embodiments of the method, the *B. microti* is propagated continuously for more than one passage. In some embodiments of the method, the *B. microti* is propagated continuously for at least 200 hours. In some embodiments of the method, the source of anti-*B. microti* IgM antibody is substantially free of IgG antibody. In some embodiments of the method, the source of anti-*B. microti* IgM antibody is from the same species as the host erythrocytes. In some embodiments of the method, the source of complement comprises a cell or cell line that is co-cultured with the host erythrocytes, and wherein the cell or cell line secretes complement into the culture medium. In some embodiments of the method, the cell or cell line is selected from the group consisting of murine PD388D1, hamster NIL-8 embryonic fibroblasts, balb/c 3T3 fibroblasts, alveolar type II epithelial cells A549, canine DH82, human THP-1, human HL60, human HeLa 229, HSB-2 lymphocytic leukemia, and monocytic leukemia cell line. In some embodiments of the method, the cell or cell line is a mammalian cell or cell line selected from the group consisting of human THP-1, human HL60, human HeLa 229, HSB-2 lymphocytic leukemia, and monocytic leukemia cell line. In some embodiments of the method, the cell or cell line is derived from human monocyte/macrophage lineage selected from THP-1, HL60 or AML-193. In some embodiments of the method, the cell or cell line is derived from human endothelial cells, human hepatic cells, human gastrointestinal cells, human epithelial cells, human alveolar cells, murine PD388D1, hamster NIL-8 embryonic fibroblasts, BALB/c 3T3 fibroblasts, or alveolar type II epithelial cells A549. In some embodiments of the method, the cell or cell line is peripheral blood mononuclear cells. In some embodiments of the method, the cell or cell line is co-cultured with the host erythrocytes either together or separately using a transwell system. In some embodiments of the method, the source of IgM antibody is selected from the group consisting of splenic lymphocytes, B cells, plasma cells, plasmablasts, and hybridomas. In some embodiments of the method, the source of complement is added exogenously to the culture medium. In some embodiments of the method, the source of complement is added by an automated device. In some embodiments of the method, the anti-*B. microti* IgM antibody is polyclonal or monoclonal. In some embodiments of the method, the doubling time of *B. microti* ranges from about 12 hours to about 24 hours.

In some embodiments, a method for continuous in vitro propagation of *B. microti*-related hemoparasites, the method comprising incubating the *B. microti*-related hemoparasites in culture medium comprising host erythrocytes in the presence of a source of complement and a source of anti-*B. microti*-related hemoparasite IgM antibody. In some embodiments of the method for continuous in vitro propagation, the *B. microti*-related hemoparasites are selected from the group consisting of *B. microti sensu lato, B. rodhaini* or "*Theileria annae*" (Spanish canine pathogen), and *B. microti*-like spp. In some embodiments of the method for continuous in vitro propagation, the anti-*B. microti*-related hemoparasite IgM antibody is polyclonal or monoclonal. In some embodiments of the method for continuous in vitro propagation, the doubling time of *B. microti*-related hemoparasites ranges from about 12 hours to about 24 hours.

In some embodiments, a propagated culture comprising *B. microti* or *B. microti*-related hemoparasites, the propagated culture comprising culture medium comprising host erythrocytes in the presence of a source of complement and a source of anti-*B. microti* IgM antibody or anti-*B. microti*-related hemoparasite IgM antibody. In some embodiments, the propagated culture is substantially free of IgG antibody. In some embodiments of the propagated culture, the host erythrocytes are selected from human, mouse hamster or other permissive host. In some embodiments of the propagated culture of the propagated culture, the source of complement is from the same species as the host erythrocytes. In some embodiments of the propagated culture, the source of anti-*B. microti* IgM antibody or anti-*B. microti*-related hemoparasite IgM antibody is from the same species as the host erythrocytes. In some embodiments, the propagated culture further comprising a cell or cell line co-cultured with the host erythrocytes, and wherein the cell or cell line secretes complement into the culture medium. In some embodiments of the propagated culture, the anti-*B. microti* IgM antibody or the anti-*B. microti*-related hemoparasite IgM antibody is polyclonal or monoclonal. In some embodiments of the propagated culture, the doubling time of *B. microti* or *B. microti*-related hemoparasites ranges from about 12 hours to about 24 hours.

Based on the teachings herein, one of ordinary skill in the art will understand how to implement the full scope of the invention. For example, based on the teachings herein, one of ordinary skill in the art will be enabled to carry out the long-term continuous propagation.

EXAMPLES

The following Examples are non-limiting and other variants contemplated by one of ordinary skill in the art are included within the scope of this disclosure.

Example 1

Hamster erythrocytes were purchased (BioChemed Services, Winchester, Va.) as whole blood with EDTA anti-coagulant and human type O erythrocytes were drawn from the inventor as whole blood with EDTA anti-coagulant at a nearby medical center at 2 week intervals.

Cultures were established and maintained in 24-well cell culture plates (Sarstedt) at 37° in either a 5% $CO_2$-in-air atmosphere (preferable) or microaerophilic stationary phase (MASP) atmosphere (5% $CO_2$, 2% $O_2$ and 93% Nitrogen) using modular incubation chambers (Billups-Rothenberg Inc., Del Mar, Calif.).

As the infection percentage would increase using the MASP atmosphere there was a regular tendency toward so-called crisis or degenerative forms, small dense intra-erythrocytic bodies. Oxygen being the most obvious variable, these cultures were moved from the MASP atmosphere to 5% $CO_2$-in-air. Surprisingly the extra oxygen returned the dominance of normal ring forms and multiple piriform merozoites overnight, suggesting perhaps the crisis forms were capable of regenerating when conditions improve. This phenomenon is also seen in vivo with late stages of hamster infections.

Example 2

Titrations were performed to determine optimal concentrations for both complement and IgM antibody using in vitro culture in 24-well well culture plates. Cultures with human erythrocytes were paired with human complement and human IgM antibody. Likewise, cultures with hamster erythrocytes were paired with hamster complement and hamster IgM antibody for optimal effect. The variable factor (complement or IgM antibody) was serially diluted in a small volume within the culture wells before adding erythrocytes and working culture (minus the variable component). For a 4-well titration a single growing culture well was washed with sterile PBS twice and the cells were added to 4 culture wells already supplemented with additional fresh erythrocytes and the titrated variable component. For an 8-well titration two culture wells were treated together to produce the 1:4 split. Stock medium was then added to bring the total volume per well to 1.25 mL After overnight incubation the various media were removed, 1 μL aliquots of the erythrocytes were diluted 1:100 in Dulbecco's PBS (DPBS) and 1 μL aliquots were spotted on 12-well IFA slides for testing. Depending upon the component being tested the slides were stained with one or more of the following: anti-IgM fluorescent conjugates, anti-complement C3 fluorescent conjugates or anti-*B. microti* IgG (with secondary conjugates). Based upon the approximate 20-24 hour in vivo doubling rate for *B. microti* the titration will generally demonstrate a plateau, followed at higher dilution by a 50% drop in fluorescent parasites per 400× microscope field.

Example 3—Complement Titration

In an attempt to follow the complement activity over time, 4 wells of culture were pooled, washed twice in PBS, then split with uninfected erythrocytes and fresh medium to produce a full 24-well culture plate with identical starting material. The cultures were supplemented with human complement, briefly mixed and returned to the incubator at various intervals (FIG. 1).

FIG. 1 shows the effect of serum complementation supplementation on *B. microti* growth. Controls without supplement throughout are depicted by (■), while another set of controls supplemented only at 4 hours with 2% complement (8×) are depicted by (●). Supplements of 0.25% complement at 4, 8 and 12 hours are depicted by (▲), while (♦) depict supplementation at 8 and 12 hours, and (□) depict 0.25% supplemented only at 12 hours. Wells of human cells and components were sampled through 24 hours and stained with IgG immune serum and anti-IgG conjugate.

The short time during which complement remained active suggested the strategy to use several-fold more than usual to avoid necessity of supplementation every 3-4 hours, but this additional complement was active less than 8 hours or led to increased erythrocyte lysis without an accompanying increase in parasite propagation. The resulting ghost erythrocytes stained indirectly with immune serum and directly with anti-C3 conjugate, suggesting complement-mediated lysis.

Example 4

The titrations described in Example 1 and 2 are used in a similar way to optimize monoclonal anti-*B. microti* IgM antibodies, both individually and in multiples. The doubling time of *B. microti* allows for single day (overnight) assays or longer (more involved, but very useful) to determine the utility of individual or mixed clones. Availability of such clones that function similarly to polyclonal antibody makes the technology more widely accessible to researchers.

Cultures with IgM monoclonal antibodies indicated that IgM monoclonal antibodies worked well and that *B. microti* can be grown successfully in serum-free medium. The medium comprised RPMI 1640-HEPES (50%) and Leibovitz L15 (50%) with glutamine, antibiotics and 2× Insulin-Transferrin-Selenium supplementation for the THP-1 cells. The doubling time was less than 24 hours (closer to 12 hours).

Example 5

One of the strains cultured and that is currently being expanded in culture came from a donor with uncomplicated babesiosis who was diagnosed with thin-smears for characteristic parasitemia and demonstrated a greater than 4-fold increase in antibody titer to B. microti by IFA testing. The thin-smear parasitemia was recorded as 0.12% (1 merozoite per 800 counted erythrocytes) and, after 8 passages (1:4 culture splits) in vitro, the infection rate was 4-6% in different culture wells. Passages at least every 3-4 days with GI strain have been consistent for over two months, but increased in percentage with every improvement in the methodology. Eventually this strain (typed as Westport strain) reached 19 passages before being frozen down, an increase of 275 billion-fold, during which the cultures were revived 3 times from frozen stocks. FIG. 2 shows thin smears of the in vitro cultivated B. microti, Westport strain, at passage 18.

Commercial availability of components and methodologies allows for more defined testing and development of treatments, pharmaceuticals and diagnostic assays for babesiosis, as well as aiding basic research on the life cycle of B. microti.

Example 6

The IgM from serum or plasma is precipitated as cryoglobulin by overnight dialysis at 2-8° C. against Dialysis Buffer (potassium phosphate buffer, 10 mM pH 5.4). Cryoglobulin was washed with cold Dialysis Buffer and then dissolved in acetate buffered saline (10 mM acetate pH 5.4). As even semi-purified IgM is notoriously unstable, it is mixed with an equal volume of IgM Stabilizing Diluent (2×—refers to 2 times more than the other examples) and maintained at 2-8° C. IgM Stabilizing Diluent (1×) consists of 20% sorbitol and 1 M glycine in 50 mM acetate buffer (pH 5.5). This stabilized IgM solution could not be used at less than a 1:50 dilution in medium due to its negative effects on the erythrocytes and its use dilution was determined by multiple in vitro culture trials using serial dilutions. In some embodiments, after longer-term experience, the use dilution has dropped from 1% to be approximately equal to the IFA titer of the stabilized IgM (1:400).

Example 7

IgM was purified from cell culture supernatant using Pierce IgM Purification Kit (44897) comprising a mannan binding protein column. 100 mL of supernatant yielded about 2 mg of IgM. IgM antibodies have lower affinities but higher avidities compared to IgG. However, IgM hybridomas tend to secrete greater amounts of antibody as compared to IgG hybridomas. The concentration of IgM secretion from hybridomas ranged from about 30 µg/ml to about 50 µg/ml. This is in contrast to IgG secretion, which ranges from about 5 µg/ml to about 20 µg/ml.

Example 8

In one experiment, of 82 clones of IgM monoclonal antibody demonstrating reactivity to B. microti, 17 clones of IgM monoclonal antibody also enabled propagation in vitro. These 17 clones of IgM monoclonal antibody supported propagation more than 3 times the background level at 2 days in culture in vitro. The 17 clones supported in vitro growth of B. microti sensu stricto and B. sensu lato strains.

Example 9

In another experiment, of 274 clones of IgM monoclonal antibody, the reactivity to B. microti of 96 clones of IgM monoclonal antibody ranged from partially/weakly reactive to strongly reactive. Of the 96 clones, 16 clones enabled propagation in vitro. The titrations of IgM supernatant ranged from undiluted to about 1:100, for example, undiluted, 1:2, 1:10, and 1:100.

Of the 16 clones, 10 clones were selected that also enabled propagation in vitro with a doubling time of 24 hours and resulting in at least 4-fold increase (as determined by immunofluorescence assays) over background levels at 3 days in in vitro culture. For the 7 clones, a 60% v/v dilution of culture supernatant was used to test in vitro propagation. The concentration of IgM in the 60% v/v diluted supernatant was about 6 µg/ml to about 12 µg/ml as determined by ELISA.

Comparisons of growth rate with polyclonal IgM and monoclonal IgM suggests that blending of clones of IgM would be beneficial, i.e., using clonal mixtures of IgM would be beneficial compared to using single IgM clones individually.

All references cited in this disclosure are incorporated herein by reference in their entireties.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of in vitro propagation of *Babesia microti*, the method comprising incubation *B. microti* in a culture medium comprising host erythrocytes in the presence of a source of complement and a source of anti-*B. microti* IgM antibody, wherein the source of the anti-*B. microti* IgM antibody is substantially free of IgG antibody, having between about 0% to 10% IgG antibody, wherein the source of complement comprises a cell or cell line that is co-cultured with the host erythrocytes and wherein the cell or the cell line secretes the complement into the culture medium.

2. The method of claim 1, wherein the *B. microti* is propagated continuously for more than one passage.

3. The method of claim 1, wherein the *B. microti* is propagated continuously for at least 200 hours.

4. The method of claim 1, wherein the source of the anti-*B. microti* IgM antibody is from the same species as the host erythrocytes.

5. The method of claim 1, wherein the cell or the cell line is selected from the group consisting of murine PD388D1, hamster NIL-8 embryonic fibroblasts, BALB/c 3T3 fibroblasts, alveolar type II epithelial cells A549, canine DH82 cell line, human THP-1 cell line, human HL60 cell line, human HeLa 229 cells, HSB-2 lymphocytic leukemia cells, and monocytic leukemia cell line.

6. The method of claim 1, wherein the cell or the cell line is a mammalian cell or mammalian cell line selected from the group consisting of human THP-1 cell line, human HeLa 229 cells, HSB-2 lymphocytic leukemia cells, and monocytic leukemia cell line.

7. The method of claim 1, wherein the cell or the cell line is derived from human monocyte/macrophage lineage selected from THP-1 cell line, HL60 cell line or AML-193 cell line.

8. The method of claim 1, wherein the cell or the cell line is derived from human endothelial cells, human hepatic cells, human gastrointestinal cells, human epithelial cells, human alveolar cells, murine PD388D1, hamster NIL-8 embryonic fibroblasts, BALB/c 3T3 fibroblasts, or alveolar type II epithelial cells A549.

9. The method of claim 1, wherein the cell or the cell line is peripheral blood mononuclear cells.

10. The method of claim 1, wherein the cell or the cell line is co-cultured with the host erythrocytes either together or separately using a transwell system.

11. The method of claim 1, wherein the source of the IgM antibody is selected from the group consisting of splenic lymphocytes, B cells, plasma cells, plasmablasts, and hybridomas.

12. The method of claim 1, wherein the source of the complement is added exogenously to the culture medium.

13. The method of claim 1, wherein the source of the complement is added by an automated device.

14. The method of claim 1, wherein the anti-*B. microti* IgM antibody is polyclonal or monoclonal.

* * * * *

UNITED STATES PATENT AND TRADEMARK OFFICE
CERTIFICATE OF CORRECTION

PATENT NO. : 10,087,412 B2  
APPLICATION NO. : 15/709253  
DATED : October 2, 2018  
INVENTOR(S) : Lee Fuller Page 1 of 1

It is certified that error appears in the above-identified patent and that said Letters Patent is hereby corrected as shown below:

On the Title Page

Right Column, Item (56), Line 14, under OTHER PUBLICATIONS, change "M" to --M on--

In the Specification

In Column 1, Line 24 (approx.), under Description of Related Art, change "*B. microti* was originally described by Victor Babes in 1885 and has been increasingly recognized as a human pathogen since then." to --Babesiosis was originally described by Victor Babes in 1885 and has been increasingly recognized as a vector-borne disease of human and veterinary importance since then.--

In Column 2, Line 17 (approx.), after "spp" insert --.--

In Column 7, Line 2, change "Don     %27t%" to --Don%27t%--

In the Claims

In Column 15, Line 20, Claim 1, change "incubation" to --incubating--

Signed and Sealed this  
Twenty-ninth Day of January, 2019

Andrei Iancu  
*Director of the United States Patent and Trademark Office*